United States Patent
Maki et al.

(10) Patent No.: US 6,452,033 B1
(45) Date of Patent: Sep. 17, 2002

(54) METHOD OF MAKING N-[2-AMINOETHYL] AMINOALKYLALKOXYSILANES WITH ETHYENEDIAMINE SALT RECYCLE

(75) Inventors: William C. Maki, Midland; Howard Bank, Freeland; Steven H. Waier; Bryan Christopher McDonald, both of Midland, all of MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 10/073,444

(22) Filed: Feb. 11, 2002

(51) Int. Cl.$^7$ ................................................ C07K 7/10
(52) U.S. Cl. ..................................................... 556/424
(58) Field of Search ........................................ 552/424

(56) References Cited

U.S. PATENT DOCUMENTS 3,146,250 A    8/1964   Speier
4,064,155 A  * 12/1977  Speier ......................... 556/424
4,448,694 A  *  5/1984  Plueddemann ............... 556/424
4,526,996 A  *  7/1985  Kilgour et al. ............... 556/424
5,446,181 A    8/1995   Uehara et al.

FOREIGN PATENT DOCUMENTS

GB        889001      2/1962
JP        56-104891   8/1981

* cited by examiner

Primary Examiner—Paul F. Shaver
(74) Attorney, Agent, or Firm—Reising, Ethington, Barnes, Kisselle, Learman & McCulloch, P.C.

(57) ABSTRACT

A method of preparing 3-[N-(2-aminoethyl)] aminoalkylalkoxysilanes in which ethylenediamine, ethylenediamine hydrochloride salt, and a suitable ω-chloroalkylalkoxysilane are fed to a reactor at a feed ratio of 3–40 moles total ethylenediamine per mole of chloroalkylalkoxysilane under reaction conditions to produce a such aminoalkylalkoxysilane. The proportions of ethylenediamine and ethylenediamine hydrochloride salt are controlled such that a phase containing the diamine salt is present in said reactor separate from a phase containing the aminoalkylalkoxysilane. Following said reaction, the salt phase is separated from the silane phase for recycle to the two phase reactor.

7 Claims, 1 Drawing Sheet

METHOD OF MAKING N-[2-AMINOETHYL] AMINOALKYLALKOXYSILANES WITH ETHYENEDIAMINE SALT RECYCLE

TECHNICAL FIELD

This invention relates to the preparation of $\omega$-[N-(2-aminoethyl)]aminoalkylalkoxysilanes. More specifically, this invention relates to the preparation of such silanes by reaction of $\omega$-chloroalkylalkoxysilane with excess ethylenediamine utilizing a recycled ethylenediamine hydrochloride salt phase stream.

BACKGROUND OF THE INVENTION

As is well known, $\omega$-[N-(2-aminoethyl)] aminoalkylalkoxysilanes have the general formula, $$R^1R^2NCH_2CH_2NR^3R^4$$

in which $R^1$, $R^2$, and $R^3$ independently are a member selected from the group consisting of a hydrogen atom or an alkoxysilane of the formula:

$$R^5Si(R^6)_{3-a}(OR^7)_a$$

in which $R^5$, $R^6$, and $R^7$ are each independently $C_{1-8}$ alkyl (including straight chain or branched alkyls) and a as 1, 2, or 3. $R^4$ is a said alkoxysilane. The $\omega$-[N-(2-aminoethyl)]aminoalkylalkoxysilanes are widely used as silane coupling agents and are effective for various polymer property modification purposes, for example, improving adhesion at an organic-inorganic interface.

These compounds are synthesized by reacting $\omega$-chloroalkylalkoxysilanes with ethylenediamine to form $\omega$-[N-(aminoethyl)]aminoalkylalkoxysilanes. Stoichiometrically, this method uses one mole of $\omega$-chloroalkylalkoxysilane and two moles of ethylenediamine for synthesizing one mole of $\omega$-[N-(2-aminoethyl)] aminoalkylalkoxysilane, with one mole of ethylenediamine monohydrochloride being formed at the same time, as shown by the following reaction scheme.

$$ClR^5Si(R^6)_{3-a}(OR^7)_a + 2NH_2CH_2CH_2NH_2 \rightarrow$$
$$NH_2CH_2CH_2NHR^5Si(R^6)_{3-a}(OR^7)_a + NH_2CH_2CH_2NH_3{}^+Cl^-$$

In the above equation $R^5$ is any alkyl group and each of $R^6$ and $R^7$ is an alkyl radical having 1 to 8 carbon atoms and a is equal to 1, 2, or 3.

In reality, the end product $\omega$-[N-(2-aminoethyl)] aminoalkylalkoxy-silane further reacts with the starting reactants $\omega$-chloroalkylalkoxysilane and ethylenediamine to form poly-alkylated products as shown below.

$$ClR^5Si(R^6)_{3-a}(OR^7)_a + NH_2CH_2CH_2NHR^5Si)$$
$$(R^6)_{3-a}(OR^7)_a + NH_2CH_2CH_2NH_2 \rightarrow NH_2CH_2$$
$$CH_2N[R^5Si(R^6)_{3-a}(OR^7)_a]_2$$
$$\{or\ (OR^7)_a(R^6)_{3-a}SiR^5NHCH_2CH_2NHR^5Si(R^6)_{3-a}$$
$$(OR^7)_a\} + NH_2CH_2CH_2NH_3{}^+Cl^-$$

This di-alkylated ethylenediamine continues to react with $\omega$-chloroalkylalkoxysilane and ethylenediamine to form the tri-alkylated product as shown below:

$$NH_2CH_2CH_2N[R^5Si(R^6)_{3-a}(OR^7)_a]_2$$
$$\{or\ (OR^7)_a(R^6)_{3-a}$$

$$SiR^5NHCH_2CH_2NHR^5Si(R^6)_{3-a}(OR^7)_a\} + ClR^5$$
$$Si(R^6)_{3-a}(OR^7)_a + NH_2CH_2CH_2$$
$$NH_2 \rightarrow (OR^7)_a(R^6)_{3-a}SiR^5NHCH_2CH_2N[R^5$$
$$Si(R^6)_{3-a}(OR^7)_a]_2 + NH_2CH_2CH_2NH_3{}^+Cl^-$$

Theoretically, this process continues until a hexaalkylated ethylenediamine product is formed, but in actuality only the mono-, di-, and tri-alkylated products are seen in detectable levels using gas chromatography analysis.

In general, a present method for preparing $\omega$-[N-(2-aminoethyl)]aminoalkyl-alkoxysilanes in a continuous flow process is as follows.

An ethylenediamine stream is co-fed to a reactor with an $\omega$-chloroalkylalkoxysilane stream of the formula:

$$ClR^5Si(R^6)_{3-a}(OR^7)_a$$

as defined above, at a feed ratio of 3–20 moles of ethylenediamine per mole of $\omega$-chloroalkylalkoxysilane. The optimum molar feed ratio of ethylenediamine to alkoxysilane is dependent upon the specific alkoxysilane used. Typically the molar feed ratio just inside the single phase region is optimum, but also depends upon the desired level of polyalkylated ethylenediamines in the product.

The ethylenediamine and $\omega$-chloroalkylalkoxysilane react as described above. A single phase effluent stream from the reactor (continuous stirred tank reactor, plug flow reactor, or combination of the two), which is a mixture of ethylenediamine, alcohol, $\omega$-[N-(2-aminoethyl)] aminoalkylalkoxysilane, and ethylenediamine monohydrochloride, is passed to a stripping and/or distillation column. In the stripping column enough ethylenediamine is removed overhead to induce a phase separation in the material remaining in the column into two liquid phases.

The alcohol mentioned above is generated in a side reaction between extraneous water impurity that enters with both the ethylenediamine and the alkoxysilane feeds. The side reaction is shown below, where b is equal to or less than a and a is equal to 1, 2, or 3.

$$-Si(R^6)_{3-a}(OR^7)_a + b^*H_2O \rightarrow -Si(R^6)_{3-a}(OR^7)_{a-b}(OH)_b + b^*R^7OH$$

The two-phase effluent stream from the distillation column is passed to a phase separator (gravity, mechanical, electrical, etc.) where the denser phase which is a mixture of ethylenediamine and ethylenediamine monohydrochloride is removed.

The lighter silane phase effluent stream from the phase separator which is mainly a mixture of ethylenediamine, alcohol, and 3-[N-(2-aminoethyl)]aminoalkylalkoxysilane, is passed to a second distillation column where the amino-ethylaminoalkylalkoxysilane is purified. The ethylenediamine and alcohol are removed from the top of the column and recycled to an ethylenediamine purification column that may also treat incoming ethylenediamine. The aminoethylaminoalkoxysilane stream is sometimes further purified in a stripping, distillation, or flash system to reduce the level of poly-alkylated ethylenediamine.

The ethylenediamine overhead stream and new ethylenediamine are also directed to the ethylene purification distillation column where alcohol is removed.

While producing a high yield of high quality alkylated ethylenediamines the prior process requires, as described above, that the contents of the reactor, the reaction mixture, be passed through a distillation column for removal of a substantial amount of ethylenediamine. The distillation operation was required before the residual reaction mixture could be separated into a product rich phase for product isolation and purification. It would be more efficient and economical to have a process in which the reaction mixture comprises two phases so that the product rich phase could be obtained without a preliminary distillation step and use of distillation equipment for that purpose. It is an object of this invention to provide such a process.

SUMMARY OF THE INVENTION

The reaction between two moles of ethylenediamine and one mole of a suitable ω-chloroalkylalkoxysilane produces an ω-[N-(2-aminoethyl)]aminoalkylalkoxysilane and a mole of ethylenediamine hydrochloride. As stated above a considerable excess of ethylenediamine is used to suppress the formation of polysilane, i.e., poly-alkylated ethylenediamine, containing products. Therefore, in a continuous process utilizing this practice, the excess ethylenediamine must be separated from the product stream and recycled to the reactor. In accordance with this invention, the byproduct ethylenediamine hydrochloride salt is also recycled to the reactor in sufficient quantity to produce two liquid phases in the reactor and in the stream flowing from it.

The two liquid phase effluent from the reactor is a mixture of ω-[N-(2-aminoethyl)]aminoalkylalkoxysilane, ethylenediamine, ethylenediamine hydrochloride, and extraneous alcohol. The stream is first conducted to a phase separation vessel rather than to a distillation column. Upon phase separation, the top bulk phase contains predominantly silane and ethylenediamine. The heavier bulk phase contains predominantly ethylenediamine hydrochloride and ethylenediamine. The heavier phase is recycled to the reactor in sufficient quantity to maintain the two phase system in the reactor and used to control the degree of polyalkylation. The balance of the heavier phase is removed from the process.

The lighter phase is transferred to a purification system consisting of a distillation and/or a flash system where ω-[N-(2-aminoethyl)]aminoalkylalkoxysilane(s) is purified by removal of the lower boiling species. Thus, the silane product is recovered in good yield and quality while the ethylenediamine is further purified by a second distillation and returned to the two phase system reactor.

The reaction is preferably conducted at a temperature in the range of about 60° to 200° C. The molar ratio of total ethylenediamine to the alkoxysilane in the reactor, including the ethylenediamine hydrochloride recycle, is at least 3 to 1 and no greater than 40 to 1.

The process of this invention is particularly useful in the manufacture of 3-[N-(2-aminoethyl)]aminopropylalkoxysilanes and 3-[N-(2-aminoethyl)]aminoisobutylalkoxysilanes. For example, 3-[N-(2-aminoethyl)]aminopropyltrimethoxysilane (or -triethoxysilane) or 3-[N-(2-aminoethyl)] aminoisobutylmethyldimethoxysilane (or -methyldiethoxysilane) can be made in high yield and quality. Depending upon product requirements these silanes can be made substantially as the mono-alkylated ethylenediamines or as mixtures of predominately the mono-alkylated product with some amounts of the di-and tri-alkylated products.

DESCRIPTION OF A PREFERRED EMBODIMENT

Figure 1:
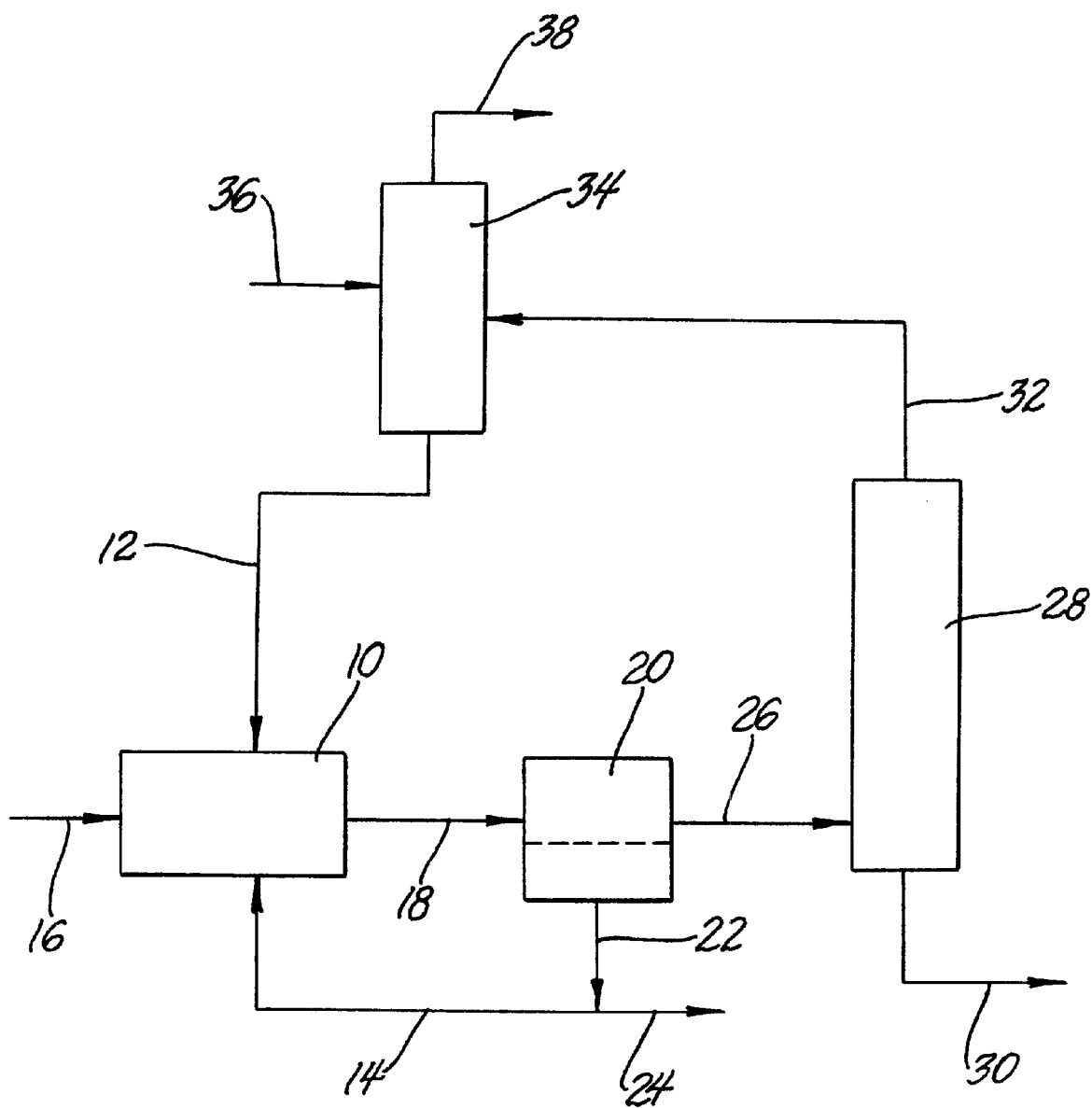
FIG. 1 is a flow diagram of the process of this invention for producing ω-[N-(2-aminoethyl)] aminoalkylalkoxysilanes.

This invention provides a novel and improved method of producing ω-[N-(2-aminoethyl)]aminoalkylalkoxysilanes such that the number of required processing steps is reduced. The method is suitable for preparing an ω-[N-(2-aminoethyl)]aminoalkylalkoxysilane of the general formula:

in which $R^1$, $R^2$ and $R^3$ independently are a member selected from the group consisting of a hydrogen atom or an alkylalkoxysilane of the formula:

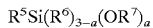

in which $R^5$, $R^6$, and $R^7$ are each independently $C_{1-8}$ alkyl and a is 1, 2, or 3. $R^4$ is a said alkylalkoxysilane.

The process comprises the establishment of a two-phase reaction system. Ethylenediamine is fed to a reactor with a chloroalkylalkoxysilane of the formula, $ClR^5Si(R^6)_{3-a}(OR^7)_a$, as defined above. At a suitable temperature of, for example, 60° to 200° C. the diamine and chloroalkylalkoxysilane react to form a desired silane product and ethylenediamine monohydrochloride salt. In accordance with this invention this byproduct salt is recycled to the reaction mixture in sufficient amount to cause the formation of a salt rich phase that is separable from the silane product containing phase. The ethylenediamine salt recycle allows the control of the formation of poly-alkylated ethylenediamine. In the case of a reaction mixture for producing 3-[N(2-aminoethyl)]aminopropyltrimethoxysilane, for example, about 1 to 15 moles of ethylenediamine salt in the recycled salt phase reactor effluent per mole of silane product is suitable for forming the two phase mixture in the reactor.

By forming the two phase reaction mixture, a product rich phase can be gravity, mechanically, or electrically separated from the ethylenediamine hydrochloride phase without an intervening distillation operation.

Referring to FIG. 1, ethylenediamine (flow stream 12), ethylenediamine salt phase (flow stream 14), and a 3-chloroalkylalkoxysilane (flow stream 16) of the formula:

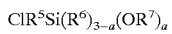

as defined above, are co-fed to reactor 10 at a feed ratio of 3–40 moles total ethylenediamine per mole of chloroalkylalkoxysilane. The proportions of ethylenediamine, stream 12, and ethylenediamine hydrochloride, stream 14 are such that a distinct phase, rich in the hydrochloride, is present in reactor 10. It is generally preferable that the molar feed ratio of ethylenediamine to ethylenediamine hydrochloride be in the range of about 1 to 20, the optimum depending on the alkoxysilane used, when the desired product is predominately a mono-alkylated ethylene diamine.

The two liquid phase effluent (flow stream 18) from the reactor, which is predominantly a mixture of ethylenediamine ω-[N-(2-aminoethyl)]aminoalkylalkoxysilane, and ethylenediaamine monohydrochloride, is passed to a phase separator vessel 20 where the bottom phase (stream 22) is split into a relatively small purge stream (stream 24) and a recycle stream 14 that is fed back to the reactor 10. Recycle stream 14 typically contains both ethylenediamine and its hydrochloride salt. The proportions depend upon the combination required for separation from the silane product containing phase. The amount of recycle is determined experimentally to produce the two-phase reactor system and effluent and to control the degree of polyalkylation.

The top phase effluent (stream 26) from phase separator 20, which is predominantly a mixture of ethylenediamine and ω-[N-(2-aminoethyl)]aminoalkylalkoxysilane, is passed to a purification system 28 where the ω-[N-(2-aminoethyl)] aminoalkylalkoxysilane is purified to varying levels. Predominantly ethylenediamine (stream 32) is removed from the silane via the top of column 28 and recycled back to a ethylenediamine purification column 34. The silane product is removed from the bottom of the column, stream 30.

In addition to the recycled ethylenediamine stream (1), a fresh ethylenediamine stream (stream 36) is fed to the system, preferentially through the ethylenediamine purification column 34 where low boiling impurities/byproducts (stream 38) are removed as the overhead stream. The purified ethylenediamine (stream 12) is then fed to the two-phase system reactor 10.

As stated, a preferred application for the process of this invention is in the production of $H_2NCH_2CH_2NHR^1SiR^3_{(3-a)}(OR^2)_a$ where $R^1$ is a propyl or isobutyl group, $R^2$ and $R^3$ are each independently methyl or ethyl groups, and a is 1, 2, or 3. Sometimes it is desired to produce essentially all monoalkylated ethylenediamine or mixtures of different degrees of polyalkylation.

EXAMPLE

Using the process equipment shown in FIG. 1, 3-[N 2-aminoethyl)]aminopropyltrimethoxysilane was prepared by reacting ethylenediamine, 3-chloropropyltrimethoxysilane, and ethylenediamine monohydrochloride at a ratio of 12 moles to 1 mole to 1.9 moles respectively, at 105° C. with a 68 minute residence time in the reactor. Titration analysis of the purified silane product stream for free amine showed the reaction to be at 99.1% conversion.

In the operation of the two-phase reactor 10, recycle stream 14 provided the recycled ethylenediamine monohydrochloride at the above stated rate of 1.9 moles per mole of 3-chloropropyltrimethoxysilane fed to the reactor. In this example, recycle stream 14 also contained about sixty percent of the ethylenediamine supplied to reactor 10.

The yield of 3-[N-(2-aminoethyl)] aminopropyltrimethoxysilane (per mole of 3-chloropropyltrimethoxysilane charged to the reactor) obtained using the salt recycle and the separate salt phase in the reactor was the same as obtained from the prior art practice of adding only salt free ethylenediamine to the reactor.

In the application of the invention to the preparation of a specific ω-[N-(2-aminoethyl)]aminoalkylalkoxysilane it is necessary to determine the reactor proportions of ethylenediamine (EDA), ethylenediamine monohydrochloride (EDA HCl) and the ω-chloroalkylalkoxysilane precursor to achieve both a desired overall EDA molar ratio and sufficient EDA HCl to obtain the two-phase system.

The invention has been described in terms of some examples and preferred embodiments. However, one skilled in the art could readily make additions and modifications in view of the teaching of this specification. Accordingly, the scope of the invention is to be considered limited only by the following claims.

What is claimed is:

1. A method of preparing ω-[N-(2-aminoethyl)] aminoalkylalkoxysilane of the formula, $R^1R^2NCH_2CH_2NR^3R^4$, in which $R^1$, $R^2$ and $R^3$ independently are a member selected from the group consisting of a hydrogen atom or an alkoxysilane of the formula, $R^5Si(R^6)_{3-a}(OR^7)_a$, in which $R^5$, $R^6$, and $R^7$ are each independently $C_{1-8}$ alkyl and a is 1, 2, or 3, and $R^4$ is a said alkoxysilane, said method comprising;

adding ethylenediamine, ethylenediamine hydrochloride salt, and ω-chloroalkylalkoxysilane of the formula, $ClR^5Si(R^6)_{3-a}(OR^7)_a$, as defined above, to a reactor at a feed ratio of 3–40 moles total ethylenediamine per mole of ω-chloroalkylalkoxysilane under reaction conditions to produce a said ω-[N-(2-aminoethyl)] aminoalkylalkoxysilane; the proportions of ethylenediamine and ethylenediamine hydrochloride salt being such that a phase containing said salt is present in said reactor separate from a phase containing said ω-[N-(2-aminoethyl)]aminoalkyl-alkoxysilane, and following said reaction separating said salt containing phase from said alkoxysilane containing phase, and returning at least a portion of said salt containing phase to said reactor as a source of a portion of said ethylenediamine and the source of said ethylenediamine hydrochloride salt.

2. A method as recited in claim 1 in which said ω-chloroalkylalkoxysilane is 3-chloropropylalkoxysilane or 3-chloroisobutylalkylalkoxysilane.

3. A method as recited in claim 1 in which said ω-chloroalkylalkoxysilane is 3-chloropropyltrimethoxysilane or 3-chloroisbutylmethyldimethoxysilane.

4. A method as recited in any of claims 1–3 wherein the molar ratio of total ethylenediamine to ω-chloroalkylalkoxysilane is in the range of 6 to 1 to 30 to 1.

5. A method of preparing $H_2NCH_2CH_2NHR^1SiR^3_{(3-a)}(OR^2)_a$ where $R^1$ is a propyl or isobutyl group, $R^2$ and $R^3$ are each independently methyl or ethyl groups, said method comprising;

adding ethylenediamine, ethylenediamine hydrochloride salt, and 3-Cl—$R^1Si(OR^2)_3$, with $R^1$ and $R^2$ as defined above, to a reactor at a feed ratio of 12–30 moles total ethylenediamine per mole of said 3-Cl—$R^1SiR^3_{(3-a)}(OR^2)_a$ under reaction conditions to produce a said $H_2NCH_2CH_2NHR^1SiR^3_{(3-a)}(OR^2)_a$; the proportions of ethylenediamine and ethylenediamine hydrochloride salt being such that a phase containing said salt is present in said reactor separate from a phase containing said $H_2NCH_2CH_2NHR^1SiR^3_{(3-a)}(OR^2)_a$, and following said reaction separating said salt containing phase from said $H_2NCH_2CH_2NHR^1Si(OR^2)_3$ containing phase, and returning at least a portion of said salt containing phase to said reactor as a source of a portion of said ethylenediamine and the source of said ethylenediamine hydrochloride salt.

6. A method as recited in claim 5 in which the temperature in said reactor is in the range of about 60° C. to 200° C. under appropriate pressure to maintain liquid phase in reactor.

7. A method as recited in claims 5 or 6 comprising returning said salt containing phase to said reactor in the amount of about 1 to 15 moles of said salt per mole of said 3-Cl—$R^1Si(OR^2)_3$ fed to said reactor.

* * * * *